United States Patent [19]
Hicswa

[11] 4,441,495
[45] Apr. 10, 1984

[54] DETACHABLE BALLOON CATHETER DEVICE AND METHOD OF USE

[75] Inventor: Daniel Hicswa, Saddle Brook, N.J.

[73] Assignee: Becton, Dickinson and Company, Paramus, N.J.

[21] Appl. No.: 408,344

[22] Filed: Aug. 16, 1982

[51] Int. Cl.$^3$ .............................................. A61B 17/12
[52] U.S. Cl. ..................................... 128/325; 604/99; 604/103
[58] Field of Search .................. 128/325, 344; 604/96, 604/99, 103

[56] References Cited

U.S. PATENT DOCUMENTS

| | | | |
|---|---|---|---|
| 3,834,394 | 9/1974 | Hunter et al. | 128/325 |
| 4,085,757 | 4/1978 | Pevsner | 128/325 |
| 4,327,734 | 5/1982 | White, Jr. | 128/325 |

*Primary Examiner*—Stephen C. Pellegrino
*Attorney, Agent, or Firm*—Richard J. Rodrick

[57] ABSTRACT

A detachable balloon catheter device comprises a hollow cannula adapted for attachment to a fluid source. An inflatable balloon is detachably connected to an end of the cannula in fluid communication therewith. A closure is adapted to seal the balloon internally after it is inflated with fluid from the source responsive to withdrawing movement of the cannula from the balloon in the proximal direction.

Use of the balloon catheter device substantially as described above to occlude a vessel is also contemplated by the present invention.

12 Claims, 7 Drawing Figures

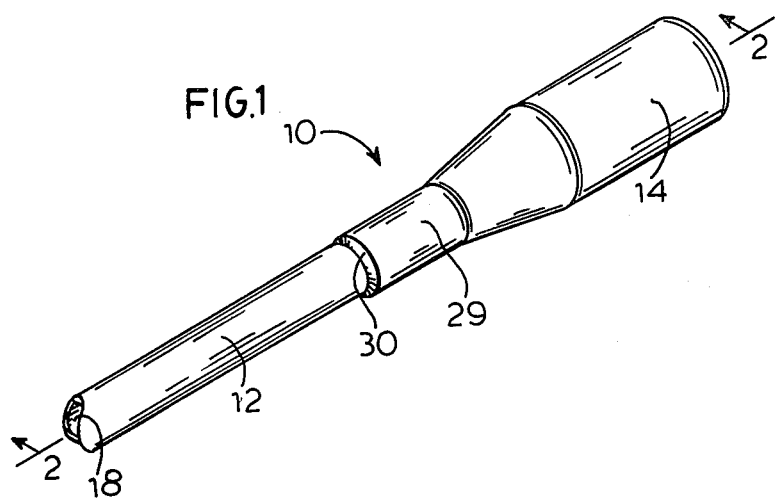
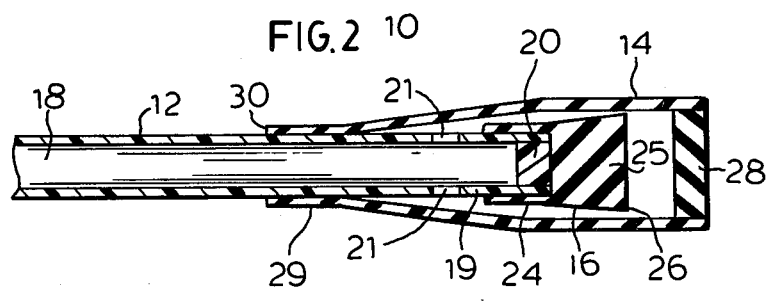
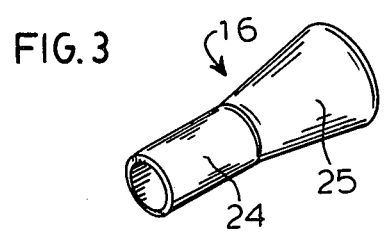

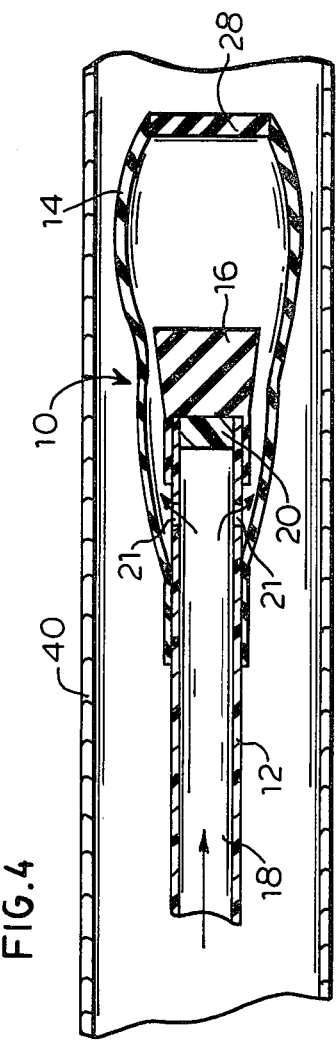

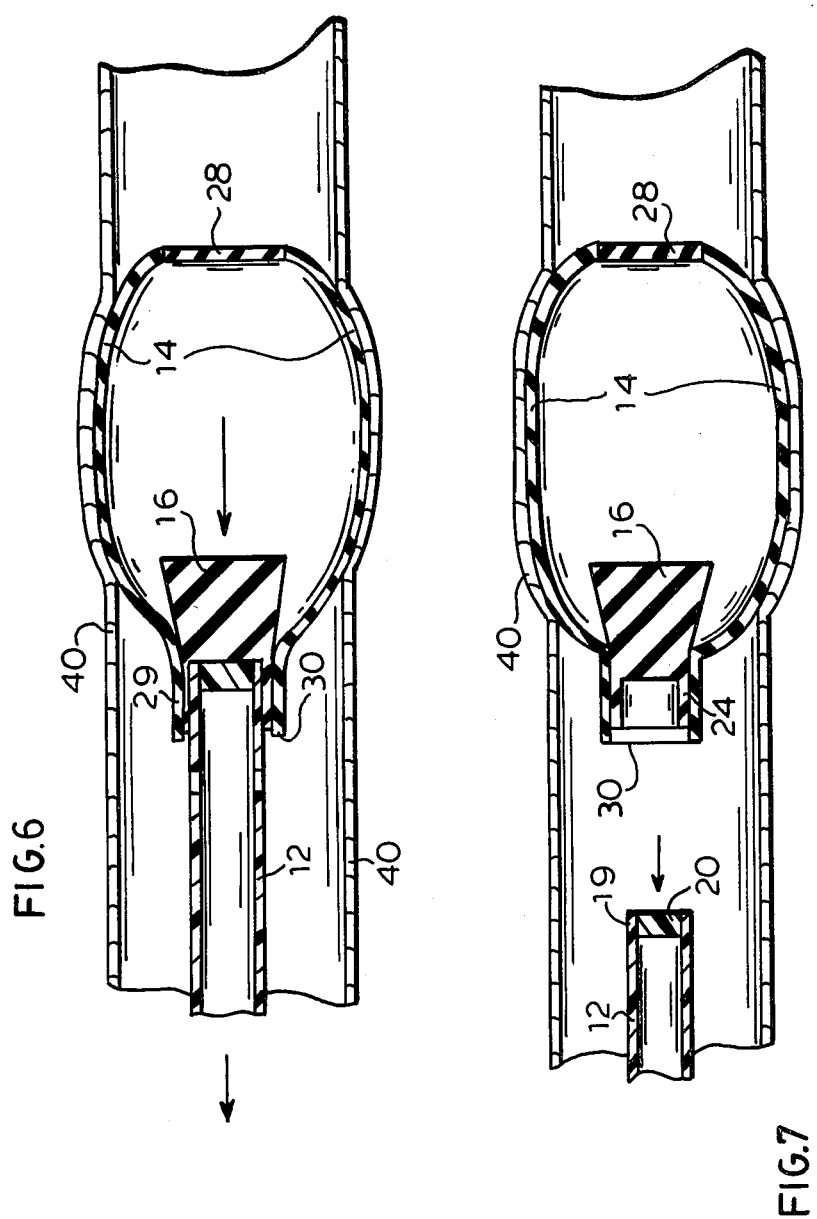

DETACHABLE BALLOON CATHETER DEVICE AND METHOD OF USE

BACKGROUND OF THE INVENTION

1. Field of the Invention

The present invention generally relates to a balloon catheter and its method of use, and more particularly, concerns a detachable balloon catheter device useful for occluding vessels, such as blood vessels, in the human body.

2. Description of the Prior Art

Balloon catheters have been used for many years to carry out medical procedures in blood vessels, body cavities and the like. Detachable balloon catheters, however, are rather recent developments directed to more particular medical procedures related to vascular occlusion or the like interventional techniques. Some of the early work in detachable balloon catheters is traced to pioneering activities of F. A. Serbinenko, M.D., and Gerard Debrun, M.D. See, e.g., Serbinenko, F. A., "Balloon Catheterization and Occlusion of Major Cerebral Vessels," *Journal of Neurosurgery*, Vol. 41, pp. 125–145, Aug. 1974, and Debrun et al., "Inflatable And Released Balloon Technique Experimentation In Dog—Application In Man," 9 Neuroradiology, p. 267, 1975. Additional activities were carried on in the 1970's by Paul Pevsner, M.D. See, e.g. Pevsner, P. H., "Micro-Balloon Catheter For Superselective Angiography And Therapeutic Occlusion," 128 *American Journal of Roentgenology*, p. 225, 1977; and U.S. Pat. No. 4,085,757.

A significant use of detachable balloon catheters is in the therapeutic occlusion of arteries. For instance, detachable silicone balloons have been employed for therapeutic embolization by R. I. White, M.D. See, e.g., White et al. "Therapeutic Embolization With Detachable Silicone Balloons," 241 *Journal of the American Medical Association*, pp. 1257–1260, Mar. 23, 1979. Detachable balloon catheters have also been used for carotid-cavernous sinus fistulas and other AV fistulas in the head. Dr. White has also employed a detachable balloon catheter for the occlusion of the internal spermatic vein in the treatment of varicoceles. At present, a detachable balloon catheter is available from Becton, Dickinson and Company, Rutherford, New Jersey, known as the B-D MINIBALLOON TM Detachable Balloon System.

One of the difficulties encountered in utilizing a detachable balloon catheter device lies in the detaching function. Initially, the inflatable balloon is attached to an introducer catheter or like cannula, and by angiographic techniques, the balloon and cannula are inserted into the artery until the balloon reaches the desired site. The balloon is inflated at that site by pressurized fluid entering the balloon through the cannula. Thereafter, it is desired to leave the inflated balloon in position while detaching the cannula. Difficulties arise because the cannula must be detached from the balloon, located at a remote site in the body, while the balloon remains in position, and inflated. Various techniques have been proposed to assure this capability of detachment while leaving the balloon inflated in situ.

One recent suggestion for improving the detachment capability of detachable balloon catheters is found in U.S. Pat. No. 4,311,146. This patented device relies upon longitudinal expansion of the balloon in the blood vessel to literally pull a valve longitudinally into the balloon inflating passage after the balloon has been inflated with sufficient fluid. The movement of this valve is described as being achieved automatically to effect a closure of the inflated balloon, whereupon the introducer catheter may be detached. It should be pointed out, however, that such automatic closure of the inflated balloon deprives the operator of flexibility in the manipulation of the balloon if it should be inflated inadvertently or if adjustments may be required in the location of the balloon at a remote site in the body. Accordingly, in this rather new field of detachable balloon catheters, improvements are still being sought which contribute to the ability to inflate the balloon, detach the catheter therefrom, while assuring that the inflated balloon remains inflated at the desired site. In addition, ease of use, simplicity of structure, economies of manufacture and operator training are factors which must be considered when improving a detachable balloon catheter device. It is to such improvements that the present invention is directed.

SUMMARY OF THE INVENTION

The balloon catheter device of the present invention comprises a hollow cannula adapted for attachment to a fluid source. An inflatable balloon is detachably connected to an end of the cannula in fluid communication therewith. Closure means are provided for sealing the balloon internally after it is inflated with fluid from the source responsive to withdrawing movement of the cannula from the balloon in the proximal direction.

In a preferred embodiment of this aspect of the invention, a detachable balloon catheter device comprises a resilient tubular cannula with a lumen extending therethrough. This cannula has a proximal portion adapted for connection to a source of external fluid and has its lumen closed at the distal end thereof. The distal portion of the cannula includes fluid passage means through the circumferential wall thereof in communication with the lumen. A plug is detachably connected to the distal portion of the cannula without blocking the fluid passage means. An inflatable balloon is detachably connected to the distal portion of the cannula covering the plug and the fluid passage means. The balloon has an opening normally in fluid-tight engagement around the cannula. The cannula is slidable proximally through the opening when the balloon is inflated to cause the plug to become disengaged from the cannula. Proximal movement of the cannula positions the plug in fluid-tight engagement in the opening interiorly of the balloon to thereby detach the cannula from the inflated balloon.

Another aspect of the present invention is the use of a detachable balloon catheter, substantially as described above, to occlude a vessel. A method of inflating and detaching the balloon from the cannula after it is inflated comprises introducing fluid from a source into the balloon to inflate same after the balloon is positioned in a vessel. The cannula is withdrawn proximally from the inflated balloon to cause closure means to seal the inflated balloon internally. Thereafter, this method includes detaching the cannula from the inflated balloon by continued proximal withdrawal.

In accordance with the principles of the present invention, a number of objectives are advantageously achieved. For instance, the present invention provides a straightforward technique for inflating a detachable balloon positioned on the cannula, while permitting ready sealing of the inflated balloon and providing for detachment of the cannula thereafter. In addition to these functional advantages, the present invention desirably minimizes functional parts and complexity of structure. The straight-forward design and structure of the present invention allows for economy of manufacture, convenience in use and minimal training for the operator who will be using this device. As a result of the structure of the present invention, cost savings to the patient should be achieved, as well as to the manufacturer.

BRIEF DESCRIPTION OF THE DRAWINGS

FIG. 1 is a perspective view illustrating the balloon end of the preferred detachable balloon catheter device of the present invention;

FIG. 2 is a cross-sectional view of the detachable balloon catheter device taken along line 2—2 of FIG. 1;

FIG. 3 is an enlarged perspective view of the preferred detachable plug utilized in conjunction with the embodiment illustrated in FIGS. 1 and 2;

FIG. 4 is a cross-sectional view of the preferred detachable balloon catheter device positioned within a blood vessel and illustrating the balloon in a state of partial inflation;

FIG. 5 is a cross-sectional view of the detachable balloon device illustrating the balloon completely inflated at the desired site in the blood vessel;

FIG. 6 is a cross-sectional view of the preferred detachable balloon catheter device illustrating the withdrawal of the cannula in a proximal direction until the plug is positioned in and seals the opening in the balloon; and FIG. 7 is a cross-sectional view of the preferred detachable balloon catheter device illustrating in sequence the sealing of the opening of the balloon and the detachment of the cannula from the balloon after it is sealed in the inflated condition.

DETAILED DESCRIPTION

While this invention is satisfied by embodiments in many different forms, there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be measured by the appended claims and their equivalents.

Adverting to the drawings, and FIGS. 1 and 2 in particular, there is illustrated the preferred detachable balloon catheter device 10 of the present invention. Device 10 is comprised of three major elements: a cannula 12, an inflatable balloon 14 and a detachable plug 16.

Turning first to cannula 12, it is preferably, but not limited to, a resilient tubular member with a lumen 18 extending therethrough. The flexibility feature is preferred inasmuch as this catheter device is expected to weave a tortuous path to a remote site inside a blood vessel. While not shown in the drawings, cannula 12 has a portion at its proximal end (nearest the operator) adapted for connection to a source of external fluid which is to be utilized for pressurizing the balloon to inflate same. Such a connection to the proximal portion of the cannula is described in U.S. Pat. No. 4,243,033. The distal end 19 of cannula 12 is provided with a stopper 20 so as to seal the lumen closed. Stopper 20 may be affixed by adhesive means, thermoplastic melting techniques or the like. On the other hand, stopper 20 may be eliminated if cannula 12 is fabricated with distal end 19 closed. In any event, for purposes of the embodiment being described, the distal end of lumen 18 should be sealed closed. Spaced a short distance proximally from the distal end of cannula 12 is a pair of holes 21 through the circumferential wall of the cannula communicating with the lumen. As will be described hereinafter, holes 21 are for the flow of pressurized fluid into the interior of balloon 14. It is appreciated that the number of such holes is a matter of choice or design; for balance, the present embodiment has two such holes.

Plug 16 is detachably connected to distal portion 19 of the cannula. As seen in FIG. 3, taken in conjunction with FIG. 1, plug 16 includes a cup-shaped portion 24 and a block-shaped portion 25. The overall configuration of plug 16 is cylindrical, with block portion 25 being preferably solid. In addition, block portion 25 is preferably tapered so that its largest diameter 26 is at its distal end thereof. Cup-shaped portion 24 is fit over distal end 19 of the cannula by frictional engagement around the outer circumferential wall of the cannula. It can be seen particularly in FIG. 2 that cup-shaped portion 24 does not cover or block holes 21 in the distal portion of the cannula.

Inflatable balloon 14 may be provided as a unitary, one-piece member. However, it is sometimes more convenient to fabricate balloon 14 with two open ends, one of which will form the distal end of the balloon catheter device. This end of the balloon may be sealed closed with a plug of material 28 similar to the material out of which the balloon is fabricated. Plug material 28 may be affixed to the distal end of balloon 14 by adhesives, thermoplastic melting or the like. A sleeve-like extension 29 tapers inwardly so that the opening 30 at the proximal end of the balloon is in a frictional and fluid-tight engagement around the outer circumferential wall of the cannula. As can be seen in FIG. 2, sleeve-like extension 29 makes contact to the cannula on the proximal side of holes 21 in the distal end of the cannula. This frictional, fluid-tight engagement of the balloon to the cannula is achieved by a controlled tight fit of opening 30 around the circumferential wall of the cannula. Additional mechanical clamps, tie-strings or the like are not required in the present invention. Moreover, it should be pointed out that plug 16 is preferably engaged only to the distal end of the cannula and remains disconnected to any interior surface of the balloon.

Suitable materials may be employed to manufacture the cannula, balloon and plug of the present invention. Elastomeric material for all of the aforementioned elements is the material of choice. For example, the flexible cannula may be made of polyurethane, polyethylene or combinations thereof. It is also understood that the cannula may have a single lumen extending therethrough, as described above in the preferred embodiment, or may have multiple lumens which may facilitate the removal of the balloon from the cannula during use. The inflatable balloon is preferably made of silicone rubber, although other elastomeric materials such as latex rubber, polyurethane and the like may be used. Furthermore, it is preferred to make the detachable plug out of the same material as the inflatable balloon for compatability purposes. To appreciate the need to have simplicity and straightforwardness of structure, a detachable balloon catheter device as herein described may be used, for example, in blood vessels up to 4 mm in diameter. For such use, the outside diameter of the uninflated balloon typically may be 1 mm. It is understood that the present invention, of course, contemplates balloons of different sizes, with the foregoing example being merely illustrative of one use of the invention herein.

FIGS. 4 to 7 depict the detachable balloon catheter device, as described above, in use in a blood vessel. Referring first to FIG. 4, detachable balloon catheter device 10 is seen inside a blood vessel 40. The proximal end of cannula 12 is connected to a source of fluid (not shown) outside of the body. As can be seen in FIG. 4, balloon 14 has been partially inflated during the insertion procedure. Fluid is delivered to the interior of balloon 14 from the fluid source outside of the body, through cannula 12 and through holes 21 in the distal portion of the cannula. Partial inflation of balloon 14 has been found to cause a "parachute" effect with the blood flow pulling the balloon and cannula, connected thereto, within the blood vessel. One technique for inserting the balloon catheter device such as described herein is found in U.S. Pat. No. 4,243,033. When the balloon is at the desired site in blood vessel 40, it is fully inflated by delivering fluid, under pressure, from the fluid source outside of the body, as mentioned above. Fluid travels along lumen 18, and since its distal end is blocked by stopper 20, fluid exits holes 21 and enters the interior of balloon 14 thereby inflating same. This inflation step is illustrated in FIG. 5. While balloon 14 is being inflated, cannula 12 and plug 16 remain in a fixed position relative to the balloon. Inflation of the balloon also has no effect on plug 16 which remains connected to the distal end of the cannula.

Once balloon 14 is properly inflated, it engages the walls of blood vessel 40 in such a manner as to provide an occlusion to thereby prevent the flow of blood therethrough past the inflated balloon. This tight engagement of the balloon is illustrated in FIGS. 5 to 7. Referring now to FIG. 6, after the balloon is fully inflated at the desired site in the blood vessel, cannula 12 is withdrawn by the operator in a proximal direction as illustrated by the arrow in FIG. 6. This proximal withdrawing movement of the cannula causes the cannula to slide outwardly, or proximally, relative to the inflated balloon which remains tightly engaged to the walls of blood vessel 40. Facilitating this sliding outward movement of the cannula is the lifting effect on sleeve-like extension 29 caused by inflation of the balloon. The fluid which inflates the balloon wets the surface of the cannula at its distal end, including the mating, junctional surfaces of the sleeve-like extension and the circumferential wall of the cannula. As a result, a lubricious effect occurs facilitating the sliding movement of the cannula through opening 30 in sleeve-like extension 29 of the balloon. Thus, when cannula 12 is withdrawn proximally by the operator, inflated balloon remains fixed in the blood vessel, and plug 16 becomes positioned within opening 30 from the interior side of the balloon. Once plug 16 is positioned within opening 30, a closure is effected thereby preventing the escape of fluid from the balloon so that the balloon may remain inflated.

With reference to FIG. 7, continued proximal withdrawal of cannula 12 by the operator causes plug 16 to become tightly engaged within opening 30 from the interior side of inflated balloon 14. The preferred tapered nature of plug 16 contributes to the effective seal of opening 30. In addition, the tapered surfaces of plug 16 serve to prevent further proximal movement of plug 16 through opening 30 in the balloon. As a result, continued proximal withdrawal of cannula 12 acts to detach distal portion 19 from cup-shaped portion 24 of the plug. Once this detachment of the cannula from the balloon and plug is accomplished, the operator may completely withdraw the cannula from the blood vessel leaving the inflated balloon at the desired site.

Thus, a detachable balloon catheter device has been provided in accordance with the present invention which readily facilitates the inflation and detachment of a balloon device which is intended to occlude a vessel. The detachable balloon catheter device herein embodies a minimal number of elements in its structure for complete operative functionability. It is economical to manufacture and straightforward to use. The catheter device herein represents a significant improvement in the field of detachable balloon catheter devices.

What is claimed is:

1. A detachable balloon catheter device comprising:
 a resilient tubular cannula with a lumen extending therethrough having a proximal portion adapted for connection to a source of external fluid and having its lumen closed at the distal end thereof, the distal portion of said cannula including fluid passage means through the circumferential wall thereof in communication with said lumen;
 a plug detachably connected to the distal portion of said cannula without blocking said fluid passage means; and
 an inflatable balloon detachably connected to the distal portion of said cannula covering said plug and said fluid passage means, said balloon having an opening normally in fluid-tight engagement around said cannula, said cannula being slidable proximally through said opening when the balloon is inflated to disengage said plug therefrom and position the plug in fluid-tight engagement in said opening interiorly of said balloon to thereby detach said cannula from said inflated balloon.

2. The device of claim 1 wherein the fluid passage means includes at least one hole through the circumferential wall of said cannula.

3. The device of claim 1 wherein said plug is connected to the distal portion of said cannula by frictional engagement around the outer circumferential wall of said cannula.

4. The device of claim 1 wherein said plug has a larger diameter than the diameter of said cannula.

5. The device of claim 4 wherein said plug is tapered, with its larger diameter being at the distal end thereof.

6. The device of claim 1 wherein said balloon includes a sleeve-like extension through which said opening extends, said sleeve-like extension being in frictional and fluid-tight engagement around the outer circumferential wall of said cannula on the proximal side of said fluid passage means.

7. The device of claim 1 wherein said plug is connected only to said cannula until it is adapted to engage the opening when the cannula is slidably withdrawn from said inflated balloon.

8. The device of claim 1 wherein said balloon and said plug are made of the same material.

9. The device of claim 8 herein said material is silicone rubber.

10. A balloon catheter device comprising:
 a hollow cannula adapted for attachment to a fluid source;

an inflatable balloon detachably connected to an end of the cannula in fluid communication therewith; and detachable closure means on the distal portion of said cannula for sealing the balloon internally after it is inflated with fluid from said source responsive to withdrawing movement of said cannula from said balloon in the proximal direction.

11. A detachable balloon catheter device comprising:

a resilient tubular cannula with a lumen extending therethrough having a proximal portion adapted for connection to a source of external fluid and having its lumen closed at the distal end thereof, the distal portion of said cannula including a plurality of holes through the circumferential wall thereof in fluid communication with said lumen;

a plug detachably connected only to the distal portion of said cannula by frictional engagement around the outer circumferential wall of said cannula without blocking said holes, said plug being tapered with its larger diameter being at the distal end thereof; and an inflatable balloon detachably connected to the distal portion of said cannula by a sleeve-like extension having an opening in frictional and fluid-tight engagement around the outer circumferential wall of said cannula on the proximal side of said holes, said cannula being slidable proximally through said opening when the balloon is inflated to cause said tapered plug to lodge in fluid-tight engagement in said opening interiorly of said balloon and become detached from said cannula whereby said cannula is detachable from said inflated balloon.

12. In the use of a detachable balloon catheter device to occlude a vessel comprising a hollow cannula adapted for attachment to a fluid source, an inflatable balloon detachably connected to an end of the cannula in fluid communication therewith, and detachable closure means on the distal portion of said cannula for sealing the balloon, a method of inflating and detaching said balloon from said cannula after it is inflated comprising:

introducing fluid from a source into said balloon to inflate same after the balloon is positioned in a vessel;

withdrawing said cannula proximally from said inflated balloon to cause said closure means to become detached from said cannula and to seal the inflated balloon internally; and thereafter detaching said cannula from said inflated balloon by continued proximal withdrawal.

* * * * *